United States Patent [19]
Werly et al.

[11] Patent Number: 5,178,536
[45] Date of Patent: Jan. 12, 1993

[54] DENTISTRY SET HAVING A HEAD INCLINED WITH RESPECT TO DRILL AXIS AND USING VISUAL CONTROL

[76] Inventors: Marc Werly, 16 rue d'Odessa, Paris, France, 75014; Victor Ringeisen, 33 rue de la Laiterie, Riedseltz, France, 67160; Paul Bleicher, 6 rue St. Georges, Haguenau, France, 67500

[21] Appl. No.: 675,928
[22] PCT Filed: Sep. 6, 1990
[86] PCT No.: PCT/FR90/00590
 § 371 Date: Jul. 8, 1991
 § 102(e) Date: Jul. 8, 1991
[87] PCT Pub. No.: WO91/03209
 PCT Pub. Date: Mar. 21, 1991

[30] Foreign Application Priority Data
Sep. 6, 1989 [FR] France .................. 89 11808

[51] Int. Cl.⁵ .................................. A61C 1/00
[52] U.S. Cl. .......................... 433/29; 433/114; 358/98
[58] Field of Search ............. 433/29, 84, 114; 358/98

[56] References Cited
U.S. PATENT DOCUMENTS

| | | | |
|---|---|---|---|
| 4,184,175 | 1/1980 | Mullane, Jr. | 433/29 |
| 4,403,956 | 9/1983 | Nakanishi | 433/29 |
| 4,727,416 | 2/1988 | Cooper et al. | 358/98 |
| 4,915,626 | 4/1990 | Lemmey | 433/29 |

FOREIGN PATENT DOCUMENTS

| | | | |
|---|---|---|---|
| 0326497 | 8/1989 | European Pat. Off. | |
| 2208902 | 8/1973 | Fed. Rep. of Germany | |
| 3045162 | 7/1982 | Fed. Rep. of Germany | |
| 3538796 | 5/1986 | Fed. Rep. of Germany | 433/29 |
| 2591094 | 6/1987 | France | |

Primary Examiner—John J. Wilson
Attorney, Agent, or Firm—Schwartz & Weinrieb

[57] ABSTRACT

Dentistry instrument with visual control having in its handle (2) pressure fluid supply lines (11, 12) as well as an optical device (14) for lighting and visualization with video transmission leading to an observation window (15), protected by a zone of turbulence generated by a pressure fluid, the instrument also including an image transmission unit and a data processing unit followed by a monitor for visualizing and processing the image.

10 Claims, 5 Drawing Sheets

DENTISTRY SET HAVING A HEAD INCLINED WITH RESPECT TO DRILL AXIS AND USING VISUAL CONTROL

BACKGROUND OF THE INVENTION

1. Field of the Invention

This invention relates to a dentistry instrument including a counter-angle drilling tool, operating by direct vision, and a computer aided visual control, and is particularly concerned with a dentistry drill.

As is conventional in the field of dentistry, reference will be made throughout this specification to a "drill" or to "drilling" where often a "mill" or "milling" is concerned.

Drilling of a dental cavity requires a vision adequate for the work to be performed. Furthermore, the deeper the zone of work, the greater is the required clarity.

Considering the limited space for operation, the dentist does not always have a clear and large enough field of vision to execute the precise work which is required, for example by the preparations for a cavity floor.

Accordingly the tactile feel of the practitioner must make up, in the majority of cases, for any defect of vision in the zone of intervention.

2. Description of the prior art

Some endoscopes have been developed, but unfortunately, they are cumbersome and of no great practical use. Moreover, it seems to be impossible to maintain such apparatus at a constant angular position with respect to the drilling instrument. Furthermore, the image formed does not have the required qualities for the required minute work.

In addition, materials recently used in dentistry demand certain requirements concerning precision and shape, if they are to be used in a reliable and lasting way, such as :
angularity of the wall,
thickness of the material.

The object of this invention is to remedy these various inconveniences by integrating an optical surveillance kit with the rotary drill used by dentists.

SUMMARY OF THE INVENTION

Thus, this invention refers to a dentistry instrument including a counter-angle drilling tool, with computer aided visual control of great definition. It contains in its handle a video micro-camera receiving an image of the operating area through an optical window, and a reflecting surface reflecting the image along the axis of the handle and transmitting it in video form with illumination by a fiber optic to an information processing set. The fiber optic terminates below the handle to aim a bundle of light beams onto the operating area. In addition, an air outlet under pressure, as well as a water pulverization outlet under pressure, form a spray directed towards the operating area.

The general inventive idea consists in integrating in a manual dentistry tool, especially a drill, a device for capturing and reconstituting images which, without any fiber optics and operating by video transmission through a light carrier using fiber optic illumination, is coupled to a computer aided modelling set, thus allowing superimposition on the image of the optimal contour of a shape as determined and drawn by the computer.

This invention results in numerous advantages, such as :

adequate usage of new synthetic materials used in dentistry,
facility of use,
precision of operation,
utilization of the current work in dentistry,
high definition of the image, which is transmitted by a video signal,
suppression of the light bundle of the fiber optic, and
use of the fiber optic for transmission of the video signal of the image.

BRIEF DESCRIPTION OF THE DRAWINGS

The technical characteristics and other advantages of the invention are described in the following description, provided as non-limiting examples of modes of implementation, and referring to the accompanying Figures, in which.

DESCRIPTION OF THE PREFERRED EMBODIMENTS

Figure 1:
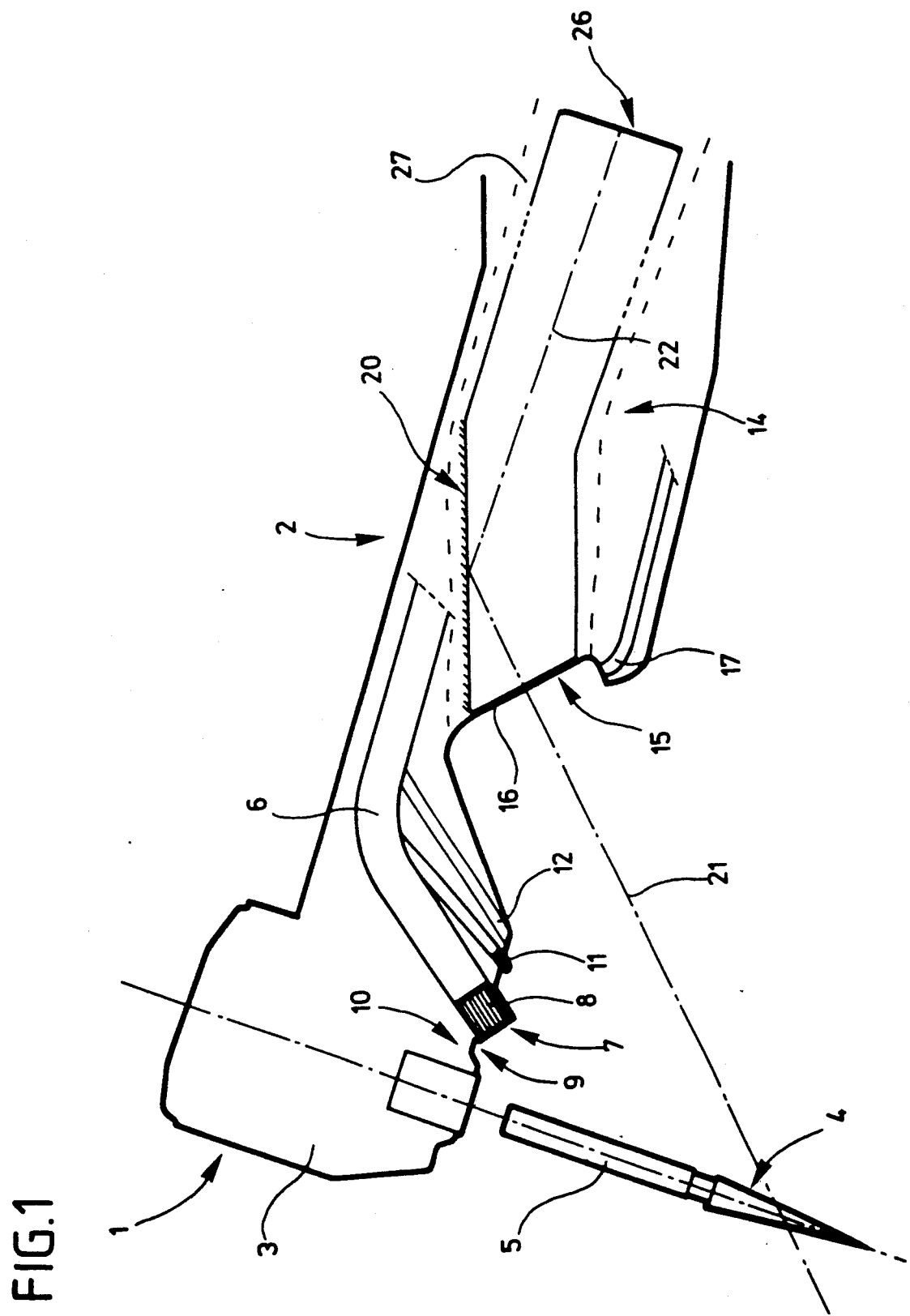
FIG. 1 is a sectional schematic view of a dentistry drill provided with visual control.

Referring first to FIG. 1, the dentistry drill 1 of the counter-angle kind has a handle 2 and a head 3 carrying a drill bit 4 provided with a shaft 5.

The handle 2 carries in its interior a fiber optic 6 which terminates below the head 3 at a protruding, adjustable illuminating head 7. This illuminating head 7 is equipped with a polarizing filter 8, in order to obtain polarized illumination.

Figure 2:
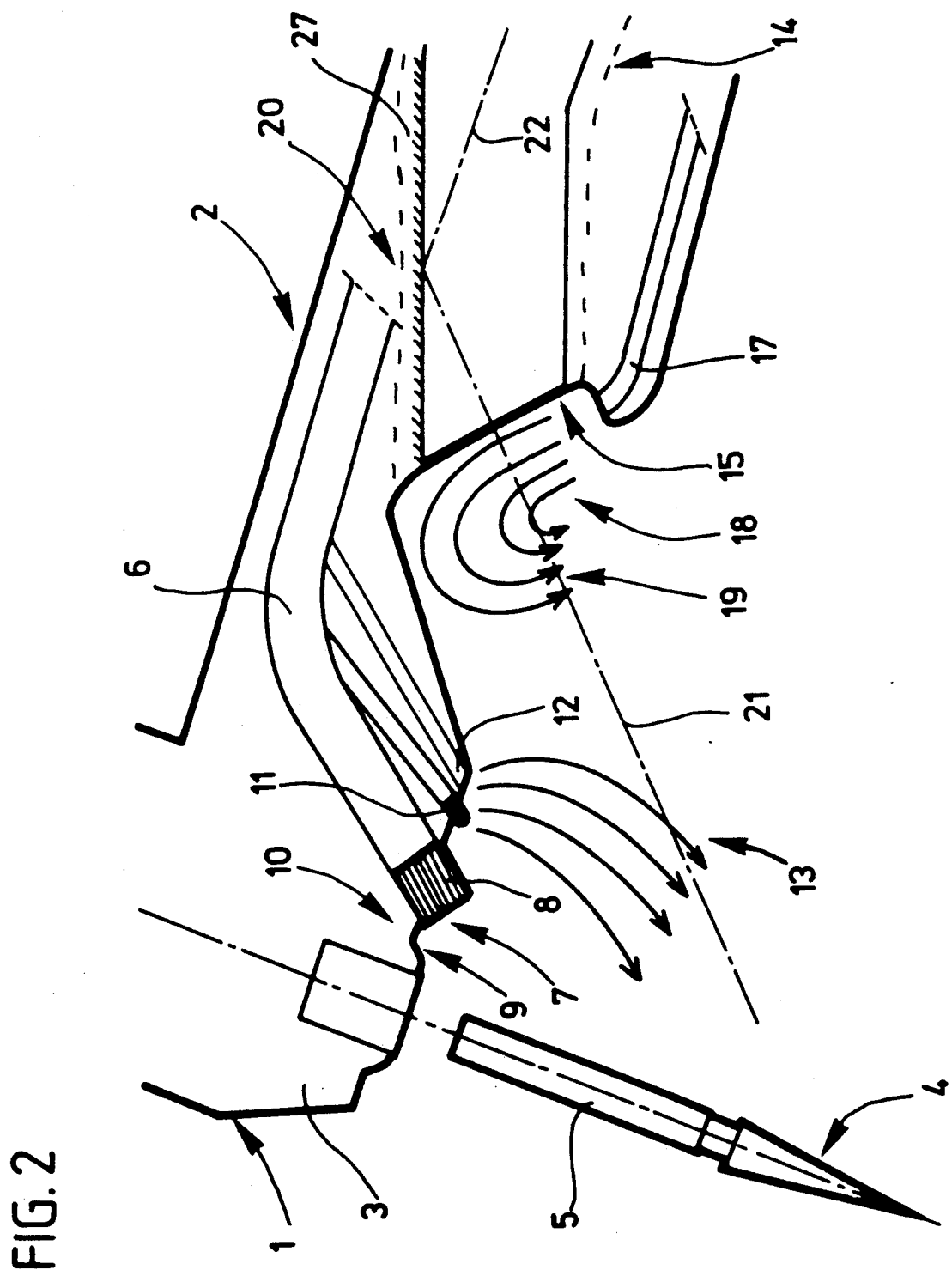
FIG. 2 is a sectional schematic view of the drill of FIG. 1, showing an over pressure area.

The illuminating head 7 is set in a slanting manner in a region where the drill head 3 merges with the handle 2 on an even zone 9 of an underface 10 of the instrument. In this zone 9, there also project from the handle 2 a water orifice 11 and an air nozzle 12 which create a pulverized jet 13 (FIG. 2).

In order to alleviate the foggy and misty effect caused by the pulverized jet 13 in the cavity of a tooth during a drilling operation, the illuminating head 7 is placed between the drill bit 4 on the one hand, and the water orifice 11 and air nozzle 12 on the other hand. Illumination behind the sheet of pulverization-nebulization is thus created so as to largely diminish any interfering or parasitic reflections, particularly those generated by water droplets. In this manner, a light curtain optically isolates the operating area from the rest of the instrument.

The handle 2 is hollow and contains an optical device 14 arranged to have a view through a window 15, which window 15 is inclined with respect to the axis of the handle 2 and is equipped with an analyzer filter 16 oriented so as to benefit from the advantages of the polarized light, for example at 90°. A conduit 17 for compressed air protrudes at the lower end of the window 15 to generate a tangential flow of air 18 (FIG. 2) which generates an over pressure zone 19, intended for expelling any suspended dirt or debris floating or lodged around or near the window 15.

Because of the inclination of the window 15 and because of the parallelism of the window 15, preferably achieved by coincidence of the optical axis of the optical device 14 with the axis of the handle 2, an upper mirror 20 reflects the image from the operating area, that is to say the image of the area next to the end of the instrument, towards optics disposed along the optical axis of the optical device 14.

The degree of inclination of the window 15 varies slightly according to the structure of the handle 2, and the inclination between the head 3 and the handle 2.

If the head 3 and the handle 2 are perpendicular to one another, the inclination of the upper mirror 20 is such that the incident optical axis 21 and the reflective optical axis 22 are each at an angle of 24° thereto.

Figure 3:
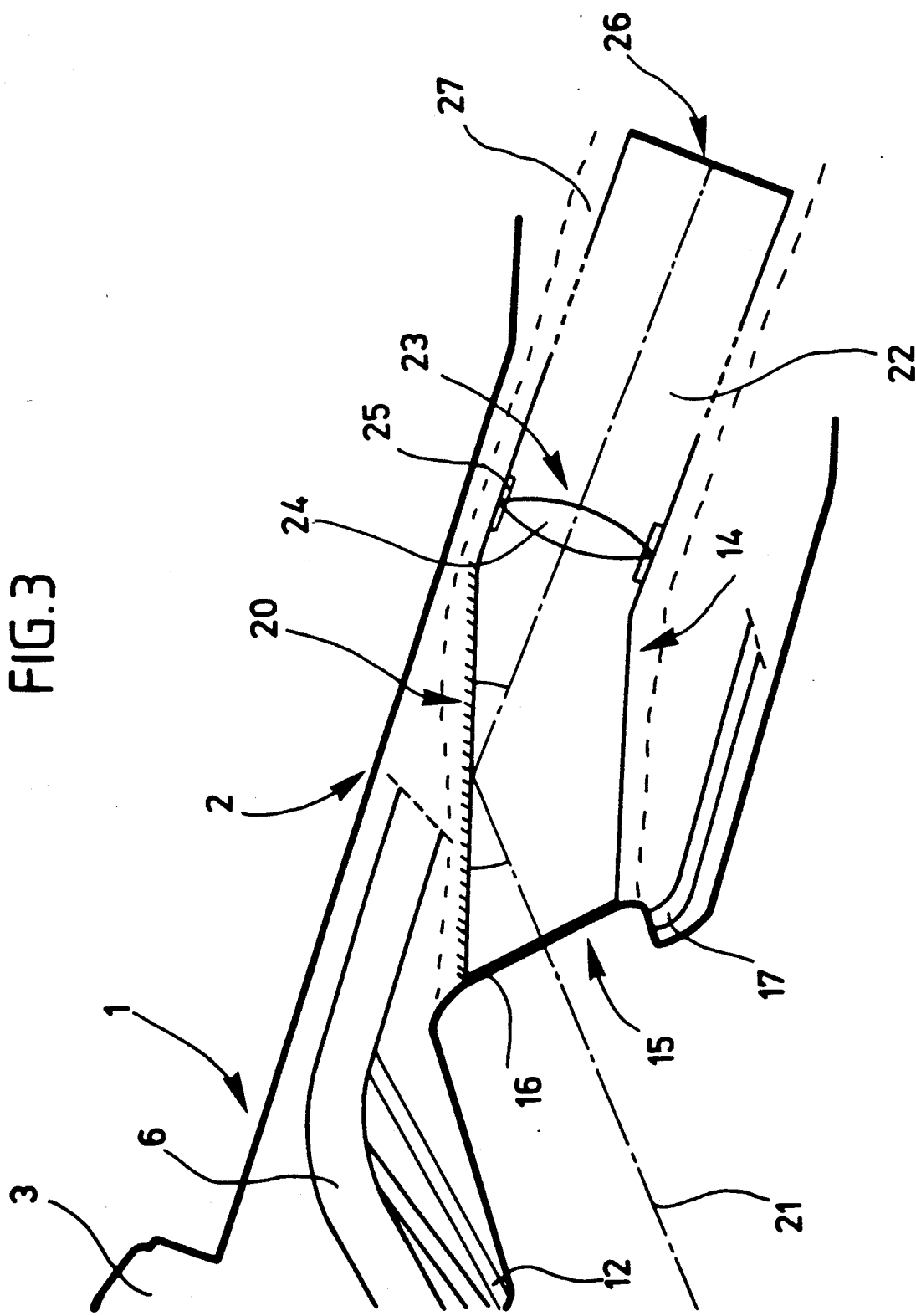
FIG. 3 is a sectional schematic view showing in greater detail an optical device disposed in a handle of the drill of FIG. 1.

The optical device 14 includes a video micro-camera 23 (FIG. 3) providing close-up views. This camera 23 is coaxial with the handle 2. Its optical axis is parallel, and preferably coaxial with the axis of the handle 2. It includes a lens 24, preferably a zoom lens, and a servo system 25 allowing it to have its focus varied electrically by a manual manipulation on the operator's part.

The lens 24 can be an interchangeable lens, interchangeable with the aid of a rapid installation and locking mechanism, for example of bayonet type.

The light sensitive surface, disposed in the focal plane of the micro-camera 23, is formed by a matrix 26 (FIGS. 1 and 5) of optoelectronic elements, for example those known under the set of initials CCD (Charge Coupled Device).

The upper mirror 20 permits any necessary change in the orientation of the optical axis.

The axis of the field of vision can be oriented by modifying the orientation of the optical axis of the mirror 20 by means of an adjustable micro-mechanism adapted to be controlled by an appropriate assembly, which is started by the action of a composite electromechanical device.

It is important to take into account that the volume, shape and dimensions of the cavity of the handle 2 used for seating the optical device 14 be such that no resonance of any harmonic frequency of the turbine or of the micromotor is possible.

Moreover, in order to allow sterilization, the optical device 14 must be suitably protected to be resistant to any manipulation and agents used. For this purpose, it is possible to provide a cavity 27 pressure-tight to at least 2 bars, which is filled with a non-oxidizing neutral gas, for example nitrogen.

In order to ensure the maintenance of a low degree of humidity, it is possible to place a salt tablet, capable of absorbing humidity, in the cavity.

For reasons of comfort and flexibility of use, the body of the instrument has an anterior part. conventionally mobile by being pivotable about a firm base, connected to a flexible composite feed in conjunction with a pivotable joint 28 (FIG. 5), which is, in turn, provided with a revolvable joint 29 intended to ensure transmission of fluids and information.

The mode of transmission of the video signal be of two possible types:
electromagnetic, by a high frequency carrier,
optical, by the modulation of an infrared diode and
transmission by the illuminating fiber optic via the revolving joint.

The sensitive matrix network of the miniature video micro-camera of the optical device is interrogated both in formation and numbering of an image by a device 30, a so-called video composite, whose video signal modulates a radiating light carrier which, for example, is infrared, and which uses for its transmission up to the optical detection device the fiber optic 6.

Figure 5:
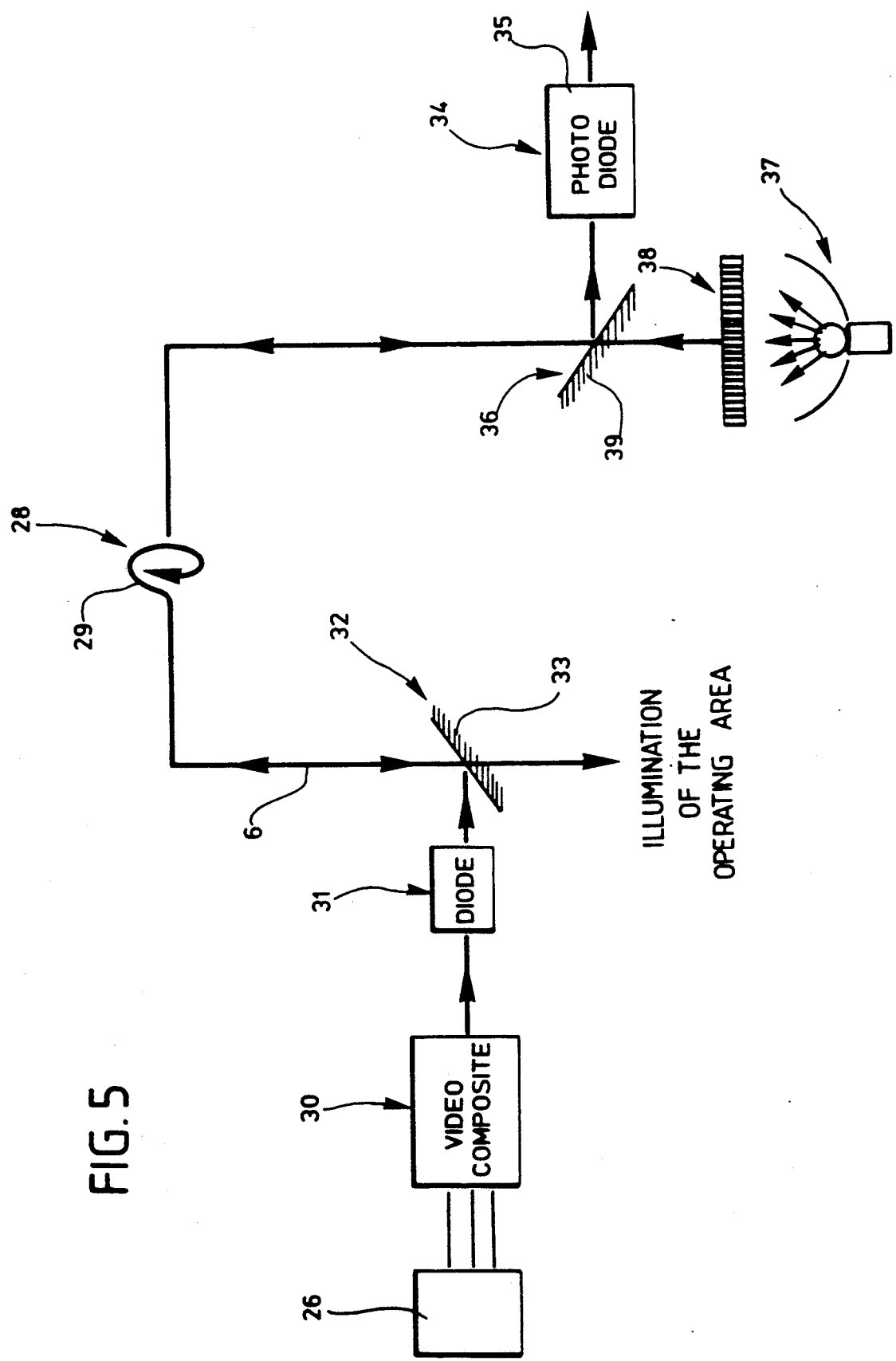
FIG. 5 is a schematic flow diagram showing the route of a video signal.

Referring to the schematic light/video transmission diagram shown in FIG. 5, a transmitting diode 31 effects modulation by a video signal of a light carrier, for example of infrared radiation, which is injected into the fiber optic 6 through a selective emission coupler 32 which can be a mirror 33 of semi-reflecting type, i.e. which is transparent for any light radiation except of the infrared type. The infrared radiation is reflected to the fiber optic 6 and is used as a support for the light carrier up to a detector 34, for example an infrared photo-diode 35, which allows modulation of the video signal before its utilization. This occurs after having appropriately isolated the infrared radiation through a selective receiving coupler 36 disposed near a distant light source 37, which latter is intended to illuminate the operating area after passing a selective infrared filter 38 and after passage through the fiber optic 6. For the filter 38, a semi-reflecting mirror 39 of the above-mentioned type can be conveniently used.

The video signal feeds a video monitor so as to form an image on a screen which is part of an information system based on a modelling program of shaping of materials on site in the dentistry domain, with a view to control visually and by computer assistance the shaping of the material.

It should be noted that for the mode of transmission of the video signal, modulation of an infrared ray is used, while for the purpose of transmission of the video signal, the fiber optic 6 is used, conveying the necessary light for illumination of the operating area.

In order to be able to transmit the signals through the pivotable joint 28 disposed between the body of the instrument and the fixed base of the handle, it is necessary to make use of an appropriate revolving joint having for example a peripheral or concentric optical coupler.

Of course, this transmission can be realized independently of the revolving joint by a separate, coaxial connection or an alternative flexible, semi-rigid or other connection. To this end, there could be utilised connection of separate fiber optics by a handle connection type, of a ratchet screw-on type, or of any other type of connection used in rapidly connectable joints.

It is possible to shift the electronic circuits described above as being on the side of the revolving joint remote from the handle into the handle so that they are on the handle side of the revolving joint. Thus, the difficulties of feeding and installation, and the inconveniences and interferences brought about by the revolving joint during the transmission of the image signal, are avoided.

Figure 4:
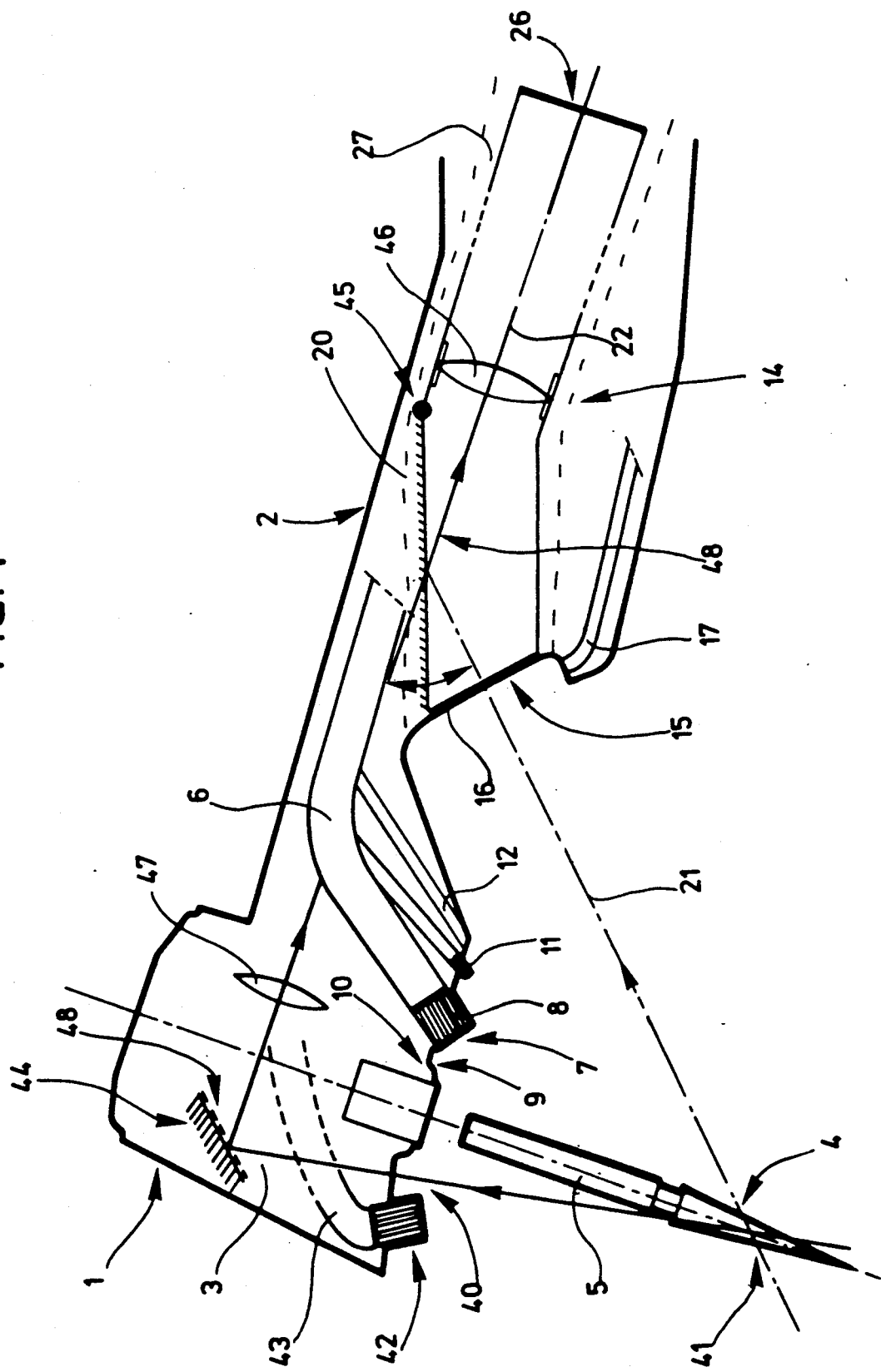
FIG. 4 is a sectional schematic view showing a second embodiment provided with two observation windows.

An embodiment of the manual instrument using direct observation, a so-called double observation instrument is shown in FIG. 4. In this embodiment, there is provided a second observation window 40 above the drill bit 4 at the tip of an inclined surface of the head 3, whose field of vision extends to a half-hidden area 41 in the shadow of the drill bit and difficult to be seen and observed by the dentist because of his unique direction of observation.

This second observation window 40 has its own illumination means 42, for example using a fiber optic 43 or annular means around the drill bit, and, if necessary, its own optical means, and means of image formation which can provide different optical characteristics from those of the optics associated with the micro-camera 23, incorporated in the handle 2. The image is reflected due to a forwardly placed reflection mirror 44, so placed as to reflect the image in the direction of the optical axis of the micro-camera, so that the so reflected image can be captured by the same micro-camera and be transmitted in the same way by a video signal.

The angle of inclination 1 remains the same because it maintains its means of observation described above. Thus, dentistry can be carried out using double observation of two different parts of the operating area or intervention zone that are behind or in front of the drill bit.

According to a manual version, the reflection mirror 20 can be moved mechanically by rocking or pivoting about an axis 45, which is controlled by a knob manually activated by the operator. The practitioner is thus able to see at will an operating area behind or in front of the drill bit. He is able to see them more closely if separate optical devices 46 and 47 of various magnifications having a fixed or variable focal length are provided.

This version can be improved by providing in place of the mirror an electrically controlled optical thin foil or plate 48, which is commercially available, and has alternatively reflecting and transparent properties. Such optical thin plates are mainly used in conjunction with liquid crystals. They become opaque and reflective under the influence of an electrical field and become transparent in the absence of an electrical field or vice versa. The dentist just has to selectively command the application of an electrical field by a simple pivoting switch or button, or by a connection button and a disconnection button for the electrical field, allowing him to view one or another image of the operating field.

It is, of course, also possible to provide such a thin plate beyond the reflection mirror 44, so as to transmit or obscure the image of that part of the working zone situated behind the drill bit.

The composite video montage and the electronic control of the application of an electrical field allow creation of a synchronized transition from one image to the other at a high frequency of successive images corresponding, for example, to that of a motion picture or of television.

The images are numbered and are transmitted in the same way by a video signal using modulation of a light carrier passed into the illuminating fiber optic 6 until a unity of processing is achieved in which the images are stored, then analyzed and processed with a view to reconstitute a unique and complete image of the operating field without any shadow and, if necessary, without seeing the drill bit or a part thereof, for example its end extremity.

It is, of course, also possible to superimpose the images by viewing them simultaneously, which is advantageous for the comfort of the practitioner.

In summation, the general idea of the invention is that it consists in integrating in a manual dentistry tool, particularly in a drill, a device for close vision and taking of close-up shots, coupled through a fiber optic that also serves for illuminating the operating area, to a video set for both formation and transmission of images, to a monitor for restoration of the images, and to a processing system including a visualization system, as well as a computer for generating and superimposing on the screen, where the image is formed, a contour or optimal shape of the work required.

According to another characteristic of this invention, it is possible to freeze the image on the screen for a predetermined length of time, and then to replace it with a new image, also frozen for the same length of time, corresponding in turn to a new view of the same operating area, so as to suppress a continuous motion of the image on the screen caused by the inevitable movements and excursions of the dentist's hand.

The image of the tooth and of its contour can then be processed with an appropriate processing program for the image, with a view to superimpose thereon a pattern or ideal contour previously indicated on the screen, and to obtain, by successive drilling operations, a perfectly prepared model, for example of the placement of a denture.

We claim:

1. A dentistry instrument providing for observation of an operating area, comprising:
    a handle having an axis defined therethrough;
    a head mounted upon one end of said handle at a predetermined angle with respect to said axis of said handle and having a dental drill mounted within said head;
    an optical observation window defined within said handle through means of which images of said operating area can be transmitted;
    a video camera disposed within said handle and in optical observation window so as to receive an image of said operating area through means of said optical observation window;
    reflecting means disposed within said handle and interposed between said optical observation window and said video camera for reflecting said image of said operating area, passing through said optical observation window, from said optical observation window to said video camera;
    fiber optic means disposed within said handle for transmitting light from a light source to said operating area for illuminating said operating area;
    a video system operatively connected to a second end of said handle, opposite said one end of said handle upon which said head is mounted, through means of a rotatable joint which permits said video system to be optically coupled to said video camera for transmission of a video signal from said video camera and for formation of a video image corresponding to said image of said operating area as transmitted through said optical observation window, reflected by said reflecting means, and received by said video camera;
    a video monitor operatively connected to said video system for displaying said video image formed by said video system;
    water spray means disposed within said handle and having an outlet defined within the vicinity of said optical observation window for spraying water toward said operating area; and
    compressed air means disposed within said handle and having an outlet defined within the vicinity of said optical observation window for exhausting compressed air outwardly toward said operating area.

2. An instrument as set forth in claim 1, wherein:
    said fiber optic mans has a terminal end which is interposed between said drill and said outlet of said water spray means.

3. An instrument as set forth in claim 1, further comprising:

polarizing means mounted upon said fiber optic means for emitting polarized light toward said operating area; and filter means mounted upon said optical observation window for eliminating any parasitic polarization resulting from light reflected from water droplets created by said water being sprayed by said water spray means.

4. An instrument as set forth in claim 1, wherein:

said video signal corresponding to said video image transmitted from said operating area is transmitted through said fiber optic means.

5. An instrument as set forth in claim 1, wherein said video system comprises:

an emitter diode for emitting modulated infrared light;

an optical emission coupler optically connected to said emitter diode for receiving said emitted modulated infrared light;

an optical receiving coupler optically connected to said optical emission coupler for receiving said modulated infrared light transmitted by said optical emission coupler, said modulated infrared light thereby being optically isolated between said optical emission coupler and said optical receiving coupler; and a photo diode optically connected to said optical receiving coupler for detecting said modulated infrared light transmitted by said optical receiving coupler.

6. An instrument as in claim 1, wherein said reflecting mean comprises:

a mirror disposed within said handle within the vicinity of said optical observation window, at a predetermined angle with respect to said axis of said handle, such that light rays incident upon, and reflected from, said mirror each subtend an angle of 25° with respect to said mirror such that said reflected light rays are transmitted along said axis of said handle which is perpendicular to an axis of said entail drill.

7. An instrument as set forth in claim 1, further comprising:

a second observation window defined within said head and disposed upon a side of said dental drill which is opposite a side upon which said optical observation window disposed within said handle is disposed;

illumination means disposed within said head for illuminating a portion of said observation area which is disposed toward said second observation window; and a refection mirror disposed within said head at a predetermined angle with respect to an axis of aid dental drill such that an observed image from said observation area is transmitted by said reflection mirror along said axis of said handle.

8. An instrument as set forth in claim 7, further comprising:

means for visually viewing different portions of said observation area by means of different images of said observation area as transmitted by said optical observation window and said second observation window.

9. An instrument as set forth in claim 1, wherein:

said reflecting means is pivotably movable within said handle so as to be movably adjusted within said handle.

10. An instrument as set forth in claim 9, wherein:

said reflecting means comprises an optical foil having optical properties which are selectively reflective or transparent.

* * * * *